US008849416B2

(12) United States Patent
Rosero

(10) Patent No.: US 8,849,416 B2
(45) Date of Patent: Sep. 30, 2014

(54) IMPLANTABLE BIO-ELECTRO-PHYSIOLOGIC INTERFACE MATRIX

(75) Inventor: Spencer Rosero, Pittsford, NY (US)

(73) Assignee: University of Rochester, Rochester, NY (US)

( * ) Notice: Subject to any disclaimer, the term of this patent is extended or adjusted under 35 U.S.C. 154(b) by 1736 days.

(21) Appl. No.: 11/579,531

(22) PCT Filed: May 4, 2005

(86) PCT No.: PCT/US2005/015380
§ 371 (c)(1),
(2), (4) Date: Jun. 24, 2008

(87) PCT Pub. No.: WO2005/107863
PCT Pub. Date: Nov. 17, 2005

(65) Prior Publication Data
US 2008/0269814 A1    Oct. 30, 2008

Related U.S. Application Data

(60) Provisional application No. 60/567,447, filed on May 4, 2004, provisional application No. 60/567,448, filed on May 4, 2004, provisional application No. 60/567,449, filed on May 4, 2004.

(51) Int. Cl.
| | | |
|---|---|---|
| A61N 1/39 | (2006.01) | |
| A61N 1/05 | (2006.01) | |
| A61N 1/375 | (2006.01) | |
| A61N 1/362 | (2006.01) | |
| A61N 1/372 | (2006.01) | |

(52) U.S. Cl.
CPC ............... *A61N 1/05* (2013.01); *A61N 1/37288* (2013.01); *A61N 1/372* (2013.01); *A61N 1/375* (2013.01); *A61N 1/37205* (2013.01); *A61N 1/3756* (2013.01); *A61N 1/362* (2013.01)
USPC ............ 607/116; 607/1; 607/2; 607/5; 607/9; 607/27; 607/36; 607/62; 607/63; 607/115

(58) Field of Classification Search
USPC .......... 607/1–2, 5, 9, 27, 36, 62–63, 115–116
See application file for complete search history.

(56) References Cited

U.S. PATENT DOCUMENTS

| | | |
|---|---|---|
| 3,554,187 A | 1/1971 | Glassner et al. |
| 3,760,332 A | 9/1973 | Berkovits et al. |

(Continued)

FOREIGN PATENT DOCUMENTS

| | | |
|---|---|---|
| CN | 1476339 A | 2/2004 |
| WO | WO 2009/002209 | 1/1998 |

(Continued)

OTHER PUBLICATIONS

TechWeb: TechEncyclopedia, *The Computer Language Company*, pp. 1-4, copyright 1981-2005.

(Continued)

*Primary Examiner* — Deborah Malamud
(74) *Attorney, Agent, or Firm* — Patent Technologies, LLC; Robert D. Gunderman, Jr.

(57) ABSTRACT

An implantable device (100) having an electronic component (110) and a biologic materials component (130). The biologic materials component has target cells in a matrix that interfaces the electronic component with the surrounding environment.

22 Claims, 2 Drawing Sheets

(56) References Cited

U.S. PATENT DOCUMENTS

| | | | |
|---|---|---|---|
| 3,842,842 A | 10/1974 | Kenny et al. | |
| 3,943,936 A | 3/1976 | Rasor et al. | |
| 4,124,029 A | 11/1978 | Penn | |
| 4,248,237 A | 2/1981 | Kenny | |
| 4,987,897 A | 1/1991 | Funke | |
| 5,154,172 A | 10/1992 | Terry, Jr. et al. | |
| 5,188,104 A | 2/1993 | Wernicke et al. | |
| 5,207,709 A | 5/1993 | Picha | |
| 5,215,086 A | 6/1993 | Terry, Jr. et al. | |
| 5,331,966 A | 7/1994 | Bennett et al. | |
| 5,351,394 A | 10/1994 | Weinberg | |
| 5,358,514 A | 10/1994 | Schulman et al. | |
| 5,404,872 A | 4/1995 | Choi | |
| 5,411,535 A | 5/1995 | Fujii et al. | |
| 5,674,251 A | 10/1997 | Combs et al. | |
| 5,707,400 A | 1/1998 | Terry, Jr. et al. | |
| 5,814,089 A | 9/1998 | Stokes et al. | |
| 5,846,188 A | 12/1998 | Palti | |
| 5,987,352 A | 11/1999 | Klein et al. | |
| 6,047,214 A | 4/2000 | Mueller et al. | |
| 6,095,148 A * | 8/2000 | Shastri et al. | 128/898 |
| 6,117,643 A | 9/2000 | Simpson et al. | |
| 6,120,460 A | 9/2000 | Abreu | |
| 6,141,588 A | 10/2000 | Cox et al. | |
| 6,168,243 B1 | 1/2001 | Abrahams | |
| 6,264,941 B1 | 7/2001 | Baetge et al. | |
| 6,330,481 B1 | 12/2001 | Van Wijk et al. | |
| 6,409,675 B1 | 6/2002 | Turcott | |
| 6,412,490 B1 | 7/2002 | Lee | |
| 6,423,001 B1 | 7/2002 | Abreu | |
| 6,438,427 B1 | 8/2002 | Rexhausen et al. | |
| 6,442,413 B1 | 8/2002 | Silver | |
| 6,445,953 B1 | 9/2002 | Bulkes et al. | |
| 6,480,733 B1 | 11/2002 | Turcott | |
| 6,496,715 B1 | 12/2002 | Lee et al. | |
| 6,512,949 B1 | 1/2003 | Combs et al. | |
| 6,522,915 B1 | 2/2003 | Ceballos et al. | |
| 6,522,926 B1 | 2/2003 | Kieval et al. | |
| 6,527,729 B1 | 3/2003 | Turcott | |
| 6,537,256 B2 | 3/2003 | Santini, Jr. et al. | |
| 6,544,193 B2 | 4/2003 | Abreu | |
| 6,551,243 B2 | 4/2003 | Bocionek et al. | |
| 6,560,486 B1 | 5/2003 | Osorio et al. | |
| 6,564,106 B2 | 5/2003 | Guck et al. | |
| 6,584,352 B2 | 6/2003 | Combs et al. | |
| 6,600,949 B1 | 7/2003 | Turcott | |
| 6,616,624 B1 | 9/2003 | Kieval | |
| 6,622,046 B2 | 9/2003 | Fraley et al. | |
| 6,647,292 B1 | 11/2003 | Bardy et al. | |
| 6,650,919 B2 | 11/2003 | Edelberg et al. | |
| 6,656,162 B2 | 12/2003 | Santini, Jr. et al. | |
| 6,721,587 B2 | 4/2004 | Gough | |
| 6,721,597 B1 | 4/2004 | Bardy et al. | |
| 6,733,485 B1 | 5/2004 | Whitehurst et al. | |
| 6,850,801 B2 | 2/2005 | Kieval et al. | |
| 6,856,835 B2 | 2/2005 | Bardy et al. | |
| 7,734,343 B2 | 6/2010 | Ransbury et al. | |
| 2002/0019584 A1 | 2/2002 | Schulze | |
| 2002/0095191 A1 | 7/2002 | Bulkes et al. | |
| 2002/0099273 A1 | 7/2002 | Bocionek | |
| 2002/0183791 A1 | 12/2002 | Denker et al. | |
| 2002/0198473 A1 | 12/2002 | Kumar | |
| 2003/0036683 A1 | 2/2003 | Kehr | |
| 2003/0153818 A1 | 8/2003 | Bocionek | |

FOREIGN PATENT DOCUMENTS

| | | |
|---|---|---|
| WO | 9826840 A1 | 6/1998 |
| WO | 9843700 A1 | 10/1998 |
| WO | 03039656 A1 | 5/2003 |
| WO | WO-2004/030706 A2 | 4/2004 |

OTHER PUBLICATIONS

Daniel A. Leung et al., Selection of Stents for Treating Iliac Arterial Occlusive Disease, Feb. 2003 JVIR, pp. 137-152, vol. 14, No. 2.

Medtronic Vascular—Racer Over-the-Wire Biliary Stent System, pp. 1-6.

Vascular Stent, Endovascularone.com: Official Homepage of Endovascular Center, pp. 1-3.

Medtronic Vascular-Bridge Extra Support Renal Stent System, pp. 1-3.

* cited by examiner

IMPLANTABLE BIO-ELECTRO-PHYSIOLOGIC INTERFACE MATRIX

RELATED APPLICATIONS

This application is a National Phase Entry of PCT/US2005/015380 filed May 4, 2005, which claims priority to provisional application Ser. Nos. 60/567,447, 60/567,448 and 60/567,449, each filed on May 4, 2004, and which are all hereby incorporated by reference in their entirety.

TECHNICAL FIELD

The present invention is generally related to implantable sensors and, more particularly, to a device for facilitating two way communication and stimulation between biologic material and electronic devices.

BACKGROUND OF THE INVENTION

The role of implantable medical devices to treat disorders of the heart, brain, nervous system and musculoskeletal system is increasingly becoming a major part of therapy and has been facilitated due to recent advances in technology. Diseases that disrupt the heart, brain, or nervous system's ability to communicate or function normally include heart rhythm disorders such as ventricular fibrillation which could be life threatening, heart block, and neurologic disorders such as epilepsy, multiple sclerosis, spinal injury, and dysautonomias. Pharmacologic therapy had traditionally been used to treat these disorders along with the use of pacemakers and defibrillators to treat heart rhythm disorders.

The treatment of brain and nervous system disorders includes deep brain stimulation methods that involve placing wires within the brain and attaching them to an implantable device to stimulate the target areas of the nervous system in order to control epilepsy, hypertension, as well as movement disorders such as Parkinson's disease. Surgical procedures have further been proposed for these disorders. For example, open brain surgery for the placement of leads (wires) that are positioned through brain tissue to reach the target sites and tunneled under the skin to a device implanted elsewhere, as well as placing wires in the heart to provide a defibrillation shock (established procedure) using the blood vessels as a conduit to reach the heart.

The treatment of epilepsy has traditionally been limited to medications or aggressive brain surgery to remove affected areas responsible for the seizures. In many ways, epilepsy has characteristics that are shared with ventricular fibrillation of the heart. Both disorders are associated with an abrupt disturbance of a regular (normal) electrical rhythm resulting in chaotic electrical activation of the heart or brain which in turn causes a seizure or sudden cardiac death.

However, current technologies, such as those described in U.S. Pat. Nos. 6,412,490 and 5,987,352, are hampered by the use of non-biological sensing elements such as electrodes or imaging based sensing. Complex steps and subsequent inherent risks are involved in obtaining venous vascular access and placing a transvenous lead in the patient population requiring defibrillation. In addition, when neurologic treatment requires an implantable lead, problems associated with lead infection, extraction when infected, as well as the mode of reaching the target organ with the least amount of trauma are important considerations.

SUMMARY OF THE INVENTION

The present invention recites an implantable device that is composed of an electronic component and a biologic materials component. The electronic component communicates (i.e., sensing and stimulation) with the biologic material it contacts. The biologic component contains cells of interest (cardiac/vascular/etc.) which are biopsied or otherwise obtained from the patient and grown in a complex collagen or other biocompatible support matrix. The matrix is lined with micron sized sensing electrodes that perform various types of sensing such as sensing of acceleration, pressure, flow, temperature, strain/shear stress and electrical discharge/signals.

The matrix is integrated to the primary circuit board that translates the signals received to a predetermined format for processing and/or relaying to another module. As many individual matrix devices as needed for a specific function can be linked in a network. Communication between devices can be accomplished via radio frequency, fiberoptic, analog electrical subcutaneous signaling, using blood as a communication medium or via direct metallic conducting media (i.e., wires) or a combination of the above.

The specificity and sensitivity of implanted and external devices is improved by using biologic tissue itself as the signal specific sensor that is integrated into the device. The biologic cells are complex and can manage multiple inputs and outputs. In addition the cells allow for miniaturization of the sensing device when integrated to an electronic circuit that then translates the individual cell responses to a digital signal.

DETAILED DESCRIPTION OF THE PREFERRED EMBODIMENT

Figure 5:
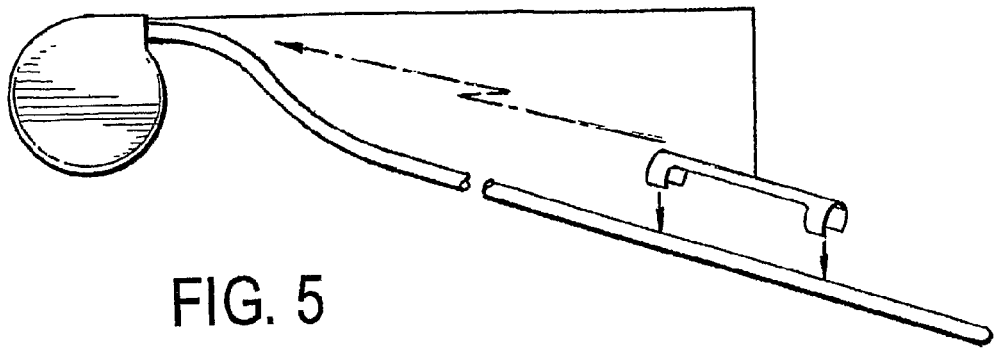

In describing a preferred embodiment of the invention as illustrated in the drawings, certain specific terminology will be used for the sake of clarity. However, the present invention is not intended to be limited by that specific terminology, and it is to be understood that the terminology includes all technical equivalents that operate in a similar manner to accomplish the same or similar result.

Figure 2:
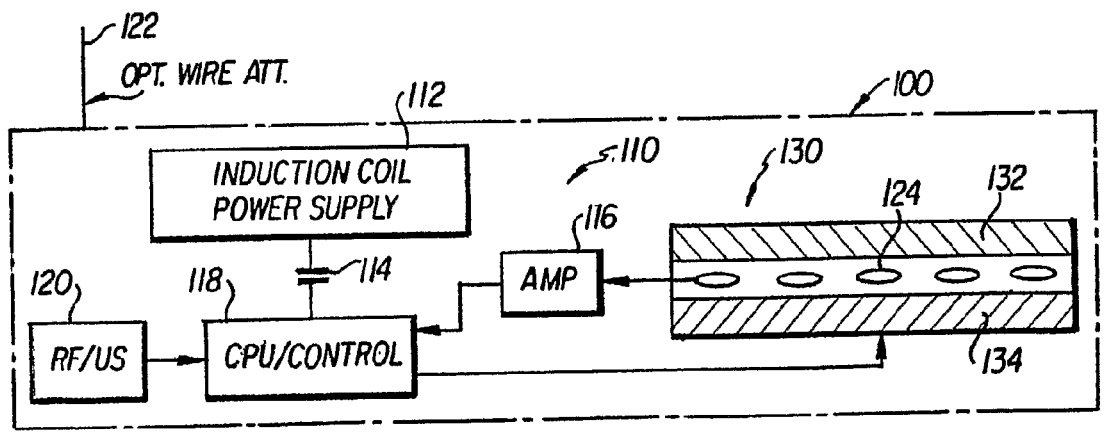
FIG. 2 is a diagram showing the electronic components and the biologic interface.
Figure 1:
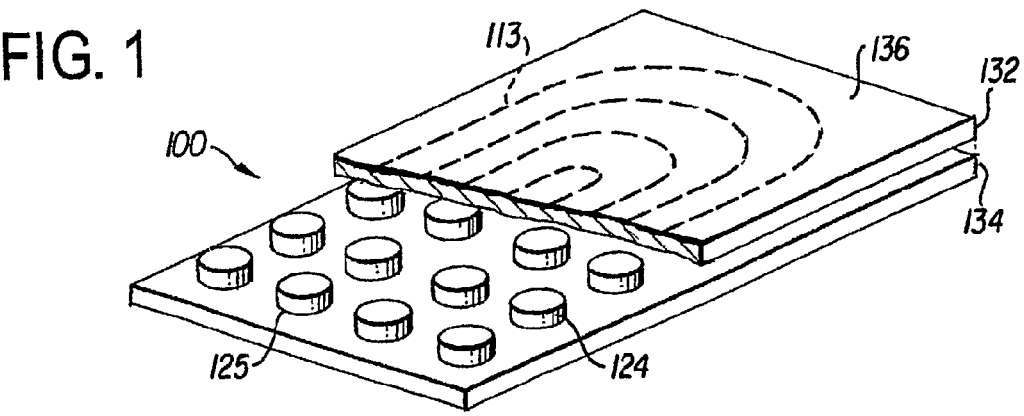
FIG. 1 is a perspective drawing of a biologic interface using a neuronal platform matrix.

Referring to the drawings, FIGS. 1 and 2 show the bio-electro-physiologic device 100 of the present invention. The device 100 includes an electronics portion 110 and a biologic materials portion or matrix interface 130. The electronics 110 include a power supply 112, capacitor 114, amplifier 116, controller 118, communication device 120 and optional wire connector 122, and electrodes or electrode array 124. The biologic interface 130 includes two layers of cells 132, 134. However, the interface 130 can have any number of layers with various geometries, including one layer or multiple cell layers.

The cell layers 132, 134 are layered along the electrode array 124 and placed within three-dimensional (i.e., multi-layered) matrices and not limited to such a layer on a two-dimensional plate. The electrodes 124 may also be arranged in a three dimensional configuration, and need not be a single layer array. The electrode array 124 and cell layers 132, 134 are placed so that the cell layers 132, 134 have a thickness of generally no more than about 0.5-1 millimeter so that the cells receive ample nutrients including oxygen exposure. The electrodes 124 are formatted as an array that forms a layer which is sandwiched between the two cell layers 132, 134.

The electrodes 124 can be positioned anywhere within the cell layers 132, 134 based on the particular application. For instance, if a single cell layer (several cells thick) is used for the biologic interface 130, the electrodes 124 can be sandwiched in the middle or positioned at the surface of that cell layer. In addition, the other electronic components of the electronics portion 110 can optionally be located within the biologic interface 130. Other electrical or non-electrical sensors 125 can also be positioned within the biologic interface 130, either together with the electrodes 124 or instead of the electrodes 124, depending on the anatomy of the site and the desired application. For instance, sensors 125 can measure pressure, flow, pH, oxygen saturation, shear forces, electrical sensing of voltage, capacitance, and current as well as stretch or pressure changes. For example, to measure blood flow or blood related substances, the sensor 125 is placed at the surface of the interface 130 so that it is exposed to the patient's blood.

In accordance with a preferred embodiment of the present invention, the power supply 112 is an induction coil 113 that is positioned on the top of the device 100 so that the device 100 is independently powered. The induction coil 113 is preferably woven into the architecture of the device 110 so as to minimize its size. However, the coil 113 can be located in any suitable location, such as inside the biologic interface 130. The capacitor 114 holds energy in storage to power the device and minimize battery use. In addition, the capacitor 114 allows for the storage and delivery of a stimulus when needed, such as a high voltage stimulus. Any level of stimulation can be provided depending on the application. The power supply 112 and/or capacitor 113 can provide cardiac defibrillation, or only power the electronic components for sensing.

The electrodes 124 and/or sensors 125 can be mounted on a flat surface for a two-dimensional basic device, as shown in FIG. 1. Or, the electrodes 124 and/or sensors 125 can be mounted in a three-dimensional device with a lattice framework in which the electrodes 124 and/or sensors 125 are positioned anywhere and the cells grown in the lattice framework to maximize surface area contact and allow for nutrient/metabolic products to traverse the matrix. The electrodes 124 and/or sensors 125 are built into the matrix architecture, so that the electrodes 124 and/or sensor 125 are integrated with the matrix interface 130. The electrodes 124 and/or sensors 125 are connected to the controller 118 and amplifier 116 by micro-welding or by wiring that extends back to the controller 118 and amplifier 116.

The controller 118 can be a processor or the like which is utilized to control operation of the device 100. The output of the controller 118 is connected to the electrodes 124 and sensors 125, and the outputs of the electrodes 124 (which can also serve as an electrical sensor) and sensors 125 are connected to the amplifier 116. The communication device 120 can be a radio frequency (RF) and/or ultrasonic transceiver, or a hard-wired transceiver that makes use of the wire connector 122. Both RAF and ultrasonic communications can be used either alone or in combination to reduce information noise for a particular application. If the device is in an electrically noisy environment, then ultrasonic communication may be more suitable.

The electronics 110 are preferably solid state microcircuitry such as MicroElectroMechanical System (MEMS) components. For instance, the electrodes 124 and/or sensors 125 are preferably in the range of several microns or several millimeters. However, any suitable size can be used depending on the application and the cells of interest as well as the signal to be detected.

The controller 118 sends various signals to the electrodes 124 to control both the sensing performed by the sensors 125 and the stimulation performed by the electrodes 124. For instance, the controller 118 sends a sense control signal that signals the sensors 125 to perform various types of sensing. The controller 118 can also send a stimulation signal that causes the electrodes 124 to generate a stimulus output of a certain voltage. The stimulus output can have a single pulse or have multiphasic waveforms that vary in frequency. The stimulation signal causes the electrodes 124 to either stimulate the target organ or stimulate or modulate the cells within the matrix interface 130.

The sensors 125 receive the signal from the controller 118 and sense patient conditions or conditions of the cell layers 132, 134. The sensors 125 output the sensed conditions in the form of an electrical signal or the cells deformation of a micro-mechanical device that senses pressure from the attached cells 132, 134. The sensors 125 transmit the sensed signal back to the controller 118 via the amplifier 116. The amplifier 116 removes ambient electrical noise and allows the detection of the physiologic signal of interest. An analog to digital (A/D) converter can also be connected between the amplifier 116 and the controller 118 to convert the signal into a format that is suitable for use by the controller 118. The controller 118 analyzes the signals received from the sensors 125 to determine the conditions sensed by the sensors 125. Based on those sensed conditions, the controller 118 may then generate a stimulation signal that is sent to the electrodes 124 to impart stimulation to the patient or cell layers 132, 134. A storage device, such as memory, may also be provided to retain data.

The controller 118 translates the signals received into a predetermined format suitable for evaluation. The controller 118 can either analyze the signal itself or forward the signal to another module (such as an infusion pump) for processing. As many individual matrix devices as needed for a specific function can be implanted in a patient and linked together to form a network. Communication between the devices is accomplished by the communications device 120 via radio frequency, fiber optic, analog electrical subcutaneous signaling using blood (which is a conductor) as the communication medium or direct metallic conducting media (i.e., wires) or a combination of the above. In addition, the communications device 120 permits the device 100 to exchange information with a computer located external to the patient. Accordingly, information can be sent from the device 100 to a computer for analysis and review by a physician. In addition, information can be sent from the computer to the device 100 to modify operation of the controller 118.

Though any number of electrodes 124 can be used, there are preferably at least two electrodes 124. The sensors 125 provide a high resolution output depending on the application (for example about 1,000 Hz for cardiac signals). The sensors 125 can perform any suitable type of sensing such as acceleration, shear stress, pressure, flow, temperature, chemical conditions and electrical discharge/signals. The accelerometer, for instance, provides data about the movement of a target organ or a person or a position of the person as well as activity of the person as a whole or the target organ. Conformational cell changes (i.e., the shape changes due to contraction or expansion) are detected by changes in pressure or shear stress in the biologic portion 130.

The biologic materials portion 130 provides an interface between the electronic components 110 to communicate (i.e., sensing and stimulation) with the biologic material it contacts. The cell layers 132, 134 integrate the device 100 with the patient's body. Further to the preferred embodiment, the cell layers 132, 134 form a matrix of intercellular tissue.

The cell layers 132, 134 are cells of interest (such as cardiac, vascular, bone, tissue, or cartilage, depending on the application) which are biopsied or otherwise obtained from the patient and grown in a complex collagen matrix. The collagen matrix is integrated with a support (such as a sponge) that can be either a metallic or inert and nonconductive framework that supports the cells and electrodes. Since the cells are cells of interest from the patient, they are able to survive once implanted. The collagen matrix is a biocompatible substance that allows the healthy growth and adhesion of cells. Collagen is preferred, but any substance can be used that has biocompatibility with the target cells and maintains cellular architecture intact while allowing cells to grow and live within its environment. The electrodes 124 and/or sensors 125 are positioned on the support and the collagen matrix introduced so that the cells grow on and around the electrodes 124 and/or sensors 125. The support preferably has a lattice or crossing pattern to enhance the growth of cells on the support.

The cell layers 132, 134 use the cellular characteristics of target cells to provide the sensing information. These cells provide sensing and individual cellular responses that can be measured by the sensors 125, such as pressure and deformation changes in cellular structure, photo-optical changes elicited by the cell, and the like. The ability to sense electrical (cardiac or neuronal electrical), chemical signals (chemoreception), and tension/pressure (flow/pressure transduction) by the device provides a broad range of clinical application for which it can be used. Devices can be individually tailored to measure a chemical of interest.

Figure 3:
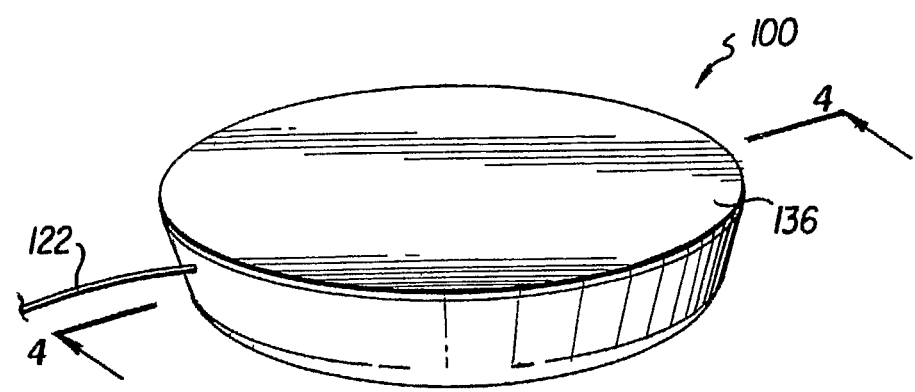
FIG. 3. is a perspective view of the bio-electro-physiologic device.
Figure 4:
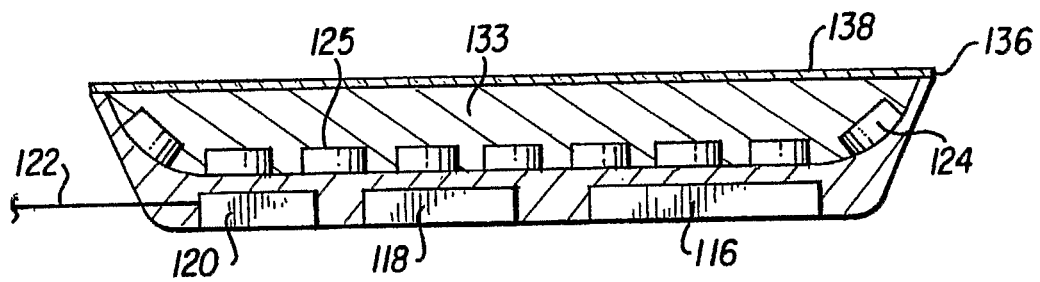
FIG. 4 is a cross section view of the bio-electro-physiologic device of FIG. 3; and, FIG. 5 is another embodiment of the device having a tubular stent-like shape attached to the lead of a pacemaker.

FIGS. 3 and 4 show one embodiment of the invention, in which the device 100 has a tapered disc shape. As best shown in FIG. 4, a single cell matrix layer 133 is provided, with electrodes 124 and sensors 125 embedded at the bottom of the layer 133. The amplifier 116, processor 118, and communications device 120 are located below the cell layer 133, and are preferably hermetically sealed separate from the cell layer 133. As further shown, the biologic interface portion 130 includes an optional semi-permeable membrane 136 that covers the cell layers. The thin semi-permeable membrane 136 allows bi-directional flow of nutrients and gas (such as oxygen) to exchange between the patient and the cell layers and allow nutrients to flow through and be exposed to the cell layers. The membrane 136 can be, for instance, a silicone or other biocompatible material that has sufficient openings or spaces (such as a fine mesh) that permit the exchange of nutrients, gas and signals, yet contain the cell matrix 133. In addition, an optional coating 138 is applied to the outer surface of cell layer 133, or to the membrane 136 (if one is provided), or to any exposed electrodes 124 or sensors 125 at the surface of the cell layer. The coating 138 inhibits the formation of scar tissue or fibrotic growth over the device 100. One preferred coating 138 is expanded polytetrafluoroethylene (ePTFE), but can also be steroids or a combination of steroids and ePTFE.

Also, growth stimulator substances can be used to facilitate the integration of the device 100 with the surrounding tissue of the patient. The growth stimulator is applied to the electrodes prior to the cells being introduced to the electrodes. The growth stimulator stimulates the growth of the cells to the electrodes.

Though the electronics 110 and biologic interface 130 are separate from one another, they can also overlap with one another. Thus, the device 100 can have any suitable shape and size. The device can be round, with the cell layers 132 forming the outer surfaces and the electronics portion 110 sandwiched there between. The device 100 can also be oval-shaped or tubular.

This device 100 does not require permanent long lead electrodes to be placed in the body tissue or vascular system. By combining cellular biologic sensors with microcircuitry, and eliminating the need for a lead, the device 100 is small and can be placed in areas that are not accessible by chronic lead placement techniques. In addition, the device can have a wire 122 that networks together multiple devices 100, though networking can also be wireless. The device can be placed transvenous as well as subcutaneous and/or within organs such as brain, gastrointestinal tract and central nervous system.

The sensing is done by the body's own cellular system to provide a response that is detected by the circuitry depending on tissue. The ability to directly select the cell type to be used as sensors provides for a small sensor since those cells can be used to sense or react to certain patient conditions without the need for additional sensors which can detect multiple substances within the body and have specific response features that can then be translated into useful information.

The cells are selected based on their ability to detect and respond to the physiologic signal of interest. For example, if a response to circulating chemical messengers such as catecholamines is required information, then skeletal muscle may be used. Accordingly, those cells eliminate the need for a separate sensor to detect the desired chemical messenger. In this setting, the muscle is biopsied from the arm or leg and placed into an environment that allows separation of the cells in an atraumatic fashion so as to minimize damage. The cells are then grown onto the device. The site of growth includes direct contact with an array of electrodes or micro-electromechanical MEMS) devices. The electrode array interface may be in a single plane or the electrodes distributed within a three-dimensional architecture so that the cells are in direct contact with a variety of electrodes. When the cell have matured and attached themselves to the electrode/MEMs, then the device is prepared for implantation within the same person from whom the cells were obtained. This minimizes scar formation and rejection.

The device may also be placed within a vessel in direct contact with blood, or within other tissue such as adipose (fat) tissue, muscle, or specific organs including the spine and nervous system. The device can monitor the integrated biologic tissue (biopsied and grown cells) and notice if there is a change in electrical activity of the cell, increased contraction or stretch activity, or metabolic activity as it responds to the physiologic signal of interest.

In this scenario, the cells respond to increase in catecholamines by increasing their frequency of firing as well as strength of contraction, which is measured by a shear stress recording sensor 125, pressure via pressure transducer 125 and the rate of change of the mechanical conformational changes. The change in shear stress/pressure and/or electrical activity (amplitude and frequency) can be detected. The electrical activity is also recorded if it is the desired signal or cellular response that is used as a marker. The device then transmits the detection to an external controller or may have its own controller 118 that either stores and/or acts on the information by emitting an electrical stimulus to inhibit or stimulate the target organ in which the device is implanted. The data may also be wirelessly communicated to another networked implanted or external device that then performs intervention that may include electrical stimulation, or trigger an infusion of a substance by an implanted or external pump.

The device 100 can also provide information for use by other medical devices, such as a cardiac ventricular assist device, to alter its flows and parameters to maximize cardiac output. The device 100 can alternatively be used to modulate blood pressure and central nervous system reflexes such as the baroreceptor reflex system from peripheral nervous system points or directly from the brain itself. It can also be used to predict events such as ventricular fibrillation or onset of seizure activity within the brain by detecting neuro-transmitter changes that can only be detected by biologic tissue.

The device 100 is able to stimulate tissue with a predetermined sub-threshold pacing and determine the response of the cell layers to obtain data regarding the cells perception of the body's physiologic processes. For example, a cell may slightly increase electrical frequency of depolarization in response to an event, but the device 100 may increase the sensitivity of detection by stimulating the cell layers 132, 134 and studying the response of the cell layers 132, 134 to the stimuli as a way of interpreting the signal. The stimulation triggers a response from the cells depending on the application. That evoked response provides information about the conditions being sensed by the cells.

The device 100 can be placed anywhere in the body, including the abdomen and brain. However, the device 100 is preferably used as a wireless sensor and stimulator, but can also be used with existing devices such as pacemakers, ICD's, deep brain stimulator devices and pain control devices. For instance, as shown in FIG. 5, the device 100 can be formed in a tubular shape that is attached to the lead of a conventional pacemaker to operate as a sensor for the pacemaker, either as part of the lead or as an additional feature of the lead.

In a preferred embodiment of the invention, one or more devices 100 are implanted in a patient as remote sensors or electrodes that communicate with a controller to operate as a defibrillator, such as described in co-pending application Ser. No. PCT/US2005/015379 entitled "Leadless Implantable Cardioverter Defibrillator" filed herewith, which claims priority to ser. no. 60/567,449 filed May 4, 2004. The controller 118 can be used as a defibrillator to impart an electrical stimulation to the patient's heart. In addition, the device 100 can be configured for use as a stent or have a stent-like shape and be integrated with electronics as described in co-pending application Ser. No. PCT/US2005/015374 entitled "Leadless Implantable Intravascular Electrophysiologic Device for Neurologic/Cardiovascular Sensing and Stimulation" filed herewith, which claims priority to ser. No. 60/567,447 filed May 4, 2004. The contents of each of these applications is incorporated herein by reference in their entirety.

It should be emphasized that the above-described embodiments of the present invention, and particularly, any preferred embodiments, are merely possible examples of implementations, merely set forth for a clear understanding of the principles of the invention. Many variations and modifications may be made to the above-described embodiments of the invention, without departing substantially from the spirit and principles of the invention. All such modifications and variations are intended to be included herein within the scope of this disclosure and the present invention and protected by the following claims.

The invention claimed is:

1. A device for implantation and detection at a target site, the device comprising:
a biologic component comprising a cell layer having cells from the target site pre-positioned on or in the device prior to implantation, wherein said pre-positioned cells are adapted to respond to a physiological signal from a patient; and
an electronic component comprising at least one sensor and at least one electrode contacting said biologic component.

2. The device of claim 1, wherein said electronic component further comprises a wireless communication device.

3. The device of claim 1, wherein said electronic component further comprises a communication device configured to network said component with other devices.

4. The device of claim 1, wherein said cell layer comprises a plurality of cells.

5. The device of claim 1, wherein said biologic component further comprises a collagen matrix and wherein said cell layer is adapted to being grown in the collagen matrix.

6. The device of claim 1, wherein said electronic component further comprises a sensor positioned within the biologic component.

7. The device of claim 6, wherein said sensor detects at least one condition of the biologic component.

8. The device of claim 7, wherein said sensor detects at least one condition of a patient.

9. The device of claim 1, wherein said electronic component further comprises an electrode positioned within the biologic component.

10. The device of claim 9, wherein said electrode stimulates the biologic component.

11. The device of claim 10, wherein said electrode stimulates a patient.

12. The device of claim 1, wherein the at least one sensor is adapted to sensing one of pressure, flow, pH, oxygen saturation, shear forces, electrical sensing of voltages, capacitance and current, stretch, and changes thereto.

13. A defibrillation device for implantation at a target site, the device comprising:
a cell layer having cells from the target site pre-positioned on or in the device prior to implantation, wherein said pre-positioned cells are adapted to respond to a physiological signal from the target site;
at least one sensor for sensing the response to the physiological signal from said cell layer: and
at least one defibrillation electrode contacting said cell layer for imparting defibrillation energy to the target site.

14. A method for detecting a physiological signal at a target site by implanting a bio-electro-physiologic interface matrix device, the method comprising:
providing a biologic component comprising a cell layer having cells from the target site pre-positioned on or in the bio-electro-physiologic interface matrix device prior to implantation, wherein said pre-positioned cells are adapted to respond to a physiological signal from a patient;
growing the biologic component within an electronic component, wherein the electronic component comprises:
at least one sensor: and
at least one electrode; and
implanting the device at the target site;
wherein said cells comprising the cell layer are selected from cells adapted to respond to the physiological signal, wherein said cells comprising the cell layer are arranged in or on said biologic component prior to the step of implanting, wherein the physiological signal originates outside the device, and wherein said at least one sensor is arranged to detect said response.

15. The method of claim 14, wherein the cell layer comprises a plurality of cells.

16. The method of claim 15, wherein the step of providing a biologic component includes obtaining the cells comprising the cell layer from a patient in which the device is to be implanted.

17. The method of claim 14, wherein the step of providing a biologic component comprises providing a collagen matrix, obtaining the cells comprising the cell layer from a patient, and growing the the cells comprising the cell layer in the collagen matrix.

18. The method of claim 14, wherein the sensor detects at least one condition of the biologic component.

19. The method of claim 14, wherein the sensor detects at least one condition of a patient.

20. The method of claim 14, wherein said electrode stimulates the biologic component.

21. The method of claim 14, wherein said electrode stimulates a patient.

22. The method of claim 14, wherein the at least one sensor is adapted to sensing one of pressure, flow, pH, oxygen saturation, shear forces, electrical sensing of voltages, capacitance and current, stretch, and changes thereto.

* * * * *